United States Patent
Ustynyuk et al.

(10) Patent No.: US 9,446,068 B2
(45) Date of Patent: Sep. 20, 2016

(54) METHOD OF PRODUCTION OF THE STABLE SELENIUM-COMPRISING PHARMACEUTICAL COMPOSITION WITH A HIGH SELENIUM LEVEL

(71) Applicant: Obschestvos S. Ogranitchennoi Otvetstvennostju "Oxygon", Moscow (RU)

(72) Inventors: Lev Aleksandrovich Ustynyuk, Moscow (RU); Shalva Iosifovitch Mardi, Binningen-BL (CH)

(73) Assignee: OBSCHESTVOS S OGRANITCHENNOI OTVETSTVENNOSTJU "OXYGON", Moscow (RU)

( * ) Notice: Subject to any disclaimer, the term of this patent is extended or adjusted under 35 U.S.C. 154(b) by 94 days.

(21) Appl. No.: 14/708,801

(22) Filed: May 11, 2015

(65) Prior Publication Data

US 2015/0238523 A1 Aug. 27, 2015

Related U.S. Application Data

(63) Continuation-in-part of application No. 13/805,472, filed as application No. PCT/RU2011/000260 on Apr. 22, 2011, now abandoned.

(51) Int. Cl.
| | |
|---|---|
| *A01N 59/02* | (2006.01) |
| *A61K 33/04* | (2006.01) |
| *A61K 31/19* | (2006.01) |
| *A61K 31/194* | (2006.01) |
| *A61K 9/00* | (2006.01) |
| *A61K 9/08* | (2006.01) |

(52) U.S. Cl.
CPC ............. *A61K 33/04* (2013.01); *A61K 9/0014* (2013.01); *A61K 9/08* (2013.01); *A61K 31/19* (2013.01); *A61K 31/194* (2013.01)

(58) Field of Classification Search
CPC ............. A61K 33/04; A61K 2300/00; A61K 31/194; A61K 31/19; A61K 9/0014; A61K 31/185; A61K 47/20; A61K 9/08; C07D 7/267; C07D 207/34; C07D 207/146; C07D 207/448; C07D 207/456; C07D 209/48; C07D 209/52; C07D 209/76; C07D 213/53; C07D 213/74; C07D 213/81
See application file for complete search history.

(56) References Cited

U.S. PATENT DOCUMENTS

| | | |
|---|---|---|
| 4,595,591 A | 6/1986 | Mardi et al. |
| 7,790,928 B1 | 9/2010 | Hechinger |

FOREIGN PATENT DOCUMENTS

| | | |
|---|---|---|
| EP | 1293498 A1 | 3/2003 |
| RU | 2366648 C2 | 9/2009 |

OTHER PUBLICATIONS

PCT Search Report from co-pending related PCT Application No. PCT/RU2011/000260, mailed Sep. 15, 2011.
Holterman, et al., Heat Capacities of Activation for the Neutral Hydrolysis of Two Acyl-Activated Esters in Water-Rich 2-n-Butozyethanol-Water Mixtures. Analysis in Terms of Pseudo-Phase-Separation Model, J. Org. Chem., 1983, 48 (22), pp. 4025-4030 (Abstract Only).

*Primary Examiner* — Nannette Holloman
(74) *Attorney, Agent, or Firm* — Thomas|Horstemeyer, LLP

(57) ABSTRACT

The present disclosure relates to the new method of producing of the stable selenium-comprising pharmaceutical compositions with a high selenium level based on the mixing of nitric acid with therapeutically effective amounts of at least two active ingredients selected from the groups consisting of 2,2-dichlorocarboxylic acids, selenium-containing compound. As a selenium-containing compound the aqueous solution of selenious acid in the amount of no more than 20%, preferably 0.5-10.0%, is used. The group of 2,2-dichlorocarboxylic acids consists 2,2-dichloropropionic acid and their homologes The chemical process is carried out by adding of the concentrated nitric acid in amount of 1.0-5.0% into 2,2-dichlorocarboxylic acid purity of at least 98.5% and completing the redox-interaction under the isothermal conditions at a temperature not higher than 70° C., preferably at 20-30° C., and then an aqueous solution of the selenious acid in an amount of not more than 20.0% (and the other components if it is necessary) is added to form the result pharmaceutical product solution. The product can also contain additional 5-20% of dimethylsulfoxide. The claimed pharmaceutical product is useful for the treating of benign, viral, premalignant, and malignant non-metastasizing skin lesions, of dysplastic lesions of visible mucous coats, fungous and other skin diseases.

6 Claims, No Drawings

METHOD OF PRODUCTION OF THE STABLE SELENIUM-COMPRISING PHARMACEUTICAL COMPOSITION WITH A HIGH SELENIUM LEVEL

CROSS-REFERENCE TO RELATED APPLICATION

This application is a continuation-in-part application which claims priority to application Ser. No. 13/805,472, filed Dec. 19, 2012, entitled "A Pharmaceutical Product, Method of Production and Method of Application of the Pharmaceutical Product," which claims priority to PCT Application No. PCT/RU2011/000260, filed Apr. 22, 2011, entitled "Medicinal Preparation, Method for Producing the Medicinal Preparation and Method for the Use Thereof" both herein incorporated by reference in their entireties. This application also claims priority to, and the benefit of, Russian patent application 2010150315, filed Dec. 9, 2010, herein incorporated by reference in its entirety.

FIELD OF THE INVENTION

The present disclosure relates to methods of producing stable selenium-comprising pharmaceutical compositions with a high selenium level useful for treating skin diseases with a topical application and also relates to prevention of Se precipitation during a long-time storage dosage form.

The medication is useful for the healing of benign, viral, premalignant, and malignant non-metastasizing skin lesions, of dysplastic lesions of visible mucous coats, fungous and other skin diseases.

BACKGROUND OF THE INVENTION

The skin is the largest organ of the human body, and its numerous diseases manifest themselves as anomalous formations, featuring a wide range of sizes, shapes and colors. Such anomalous formations are often cosmetically unappealing, but only in seldom cases represent a danger to life.

The standard therapy used for skin tumor treatment is determined by many factors, including the exact histologic subtype, the tumor size, the growth characteristics and the anatomic location. Treatment is also determined by the previous treatment received, current medical problems and the patient's expectations.

Treatment options may be categorized as surgical and non-surgical. Surgical treatments include laser or electrodessication and curettage, simple or wide local excision of the lesion or Mohs micrographic surgery. Non-surgical treatments include radiation therapy, photodynamic therapy, cryotherapy and topical drug therapy.

One of the prevailing methods of tumor skin lesions treatment with a topical application involves the use of a drug with sufficient corrosive activity consisting of mineral and organic acids. Practically almost all aggressive chemicals can show necrotizing action on a skin depending on the concentration and quantity of chemicals, the mechanism of their influence, degree of penetration and duration of exposure.

Topical applications are oftentimes preferred over laser therapy or cryotherapy because they can minimize any potential systemic adverse effects of drug, are easier to conduct and less expensive.

U.S. Pat. Nos. 4,595,591 and 5,573,786 describe compositions consisting of nitric acid and nitrous acid or metal nitrite. However, adequate results using SOLCODERM™ (a medication manufactured and distributed by Solco Basel AG (Switzerland)) are achieved only if the recommended storage temperature and the use-by dates indicated are observed as accurately as possible, since fluctuations in the nitrite concentration during a long-time storage may severely decrease the effectiveness of medication. In addition, it has been observed that medication such as SOLCODERM™, when inactive, present an increased danger of side effects.

U.S. Pat. No. 7,128,903 suggests a preparation, consisting of trichloracetic, hydrochloric and formic acids.

U.S. Pat. Nos. 4,380,549, 5,091,171 and 5,407,958 suggest preparations based on alpha-hydroxycarboxylic acid including salicylic acid.

In prior EP No. 1 293 498 entitled "Selenium complex with haloethanoic acid or its anhydride, and use thereof in the topical treatment of neoplasms," Mardi et. al. described and claimed the compounds which can have the therapeutic efficacy in topical treatment of inflammatory skin conditions.

The closest analogue of the present disclosure in terms of the technical characteristics is our most recent RU 2366648 entitled "The product of interaction between selenious dioxide and aliphatic haloid carboxylic acids, the method of production preparation and the method of treatment of benign, viral, premalignant, and malignant non-metastasizing skin lesions, of dysplastic lesions of visible mucous coats, fungous and other skin diseases." It was described here that aliphatic alpha-haloidcarboxylic acids and related compounds are therapeutically effective for topical treatment of various cosmetic conditions and dermatologic disorders including more than 70 nosologies of skin lesions in humans. According to this patent, the preparation of complex compounds of general formula $H_2SeO_3 xRCXY(CH_2)_m COOH$ is achieved by heating selenious dioxide with aliphatic haloid carboxylic acids, followed by filtering.

The disadvantages of this method are the instability of solutions of the semi-finished product (substance) and the dosage band, low and uncontrollable concentration of selenium and the impossibility of its regulation. The compositions recommended for the practical application, were resolving while in storage, and the process was accompanied by the selenium precipitation, which is unacceptable.

Some of the disadvantages of the pharmaceutical composition under prior art usually were opened only after long-term tests and in practical applications Drugs are products whose quality the consumer can not appreciate at its true value. Therefore, a guarantee of quality, safety and efficacy of drugs is the responsibility of the manufacturer and is provided by checking these indicators through at all stages of the drug life cycle.

Precipitation when storing pharmaceutical substances is a typical example of chemical incompatibility. The products of such reactions lose most of their therapeutic effects probably because the penetration in skin and distribution of the active ingredients to the target site are generally diminished.

Incompatibility ingredients of drugs are often successfully addressed using adjuvants or special kinds of packing.

The above brief review clearly indicates that there is an urgent need to develop a new, simple, rapid, highly safe, highly effective method of production of the pharmaceutical compositions for topical treatment of skin diseases.

The present disclosure aimed to achieve the above objectives will now be described in more detail with reference to following examples that are merely illustrative of the compositions and methods of the present invention and are not intended to be limiting.

SUMMARY OF THE INVENTION

The present disclosure relates to the surprising discovery that the right order of mixing ingredients can provide the stability of selenium-comprising pharmaceutical compositions even with a high selenium level during the entire life cycle of the drug.

The present disclosure also relates to the chemical process carried by interaction between alpha, alpha-dichlorocarboxylic acid, stabilized by nitric acid, and selenious acid aqueous solution as the selenium-containing compound.

The present disclosure also relates to a method of the stable selenium-comprising pharmaceutical compositions with a high selenium level production wherein dichloroacetic acid or 2,2-dichloro-butyric acids or the other members of the homologous series subjected to a similar stabilization can be used as an alternative to alpha, alpha-dichloropropionic acid.

The present disclosure also relates to the further development methods of preparation drug with improved therapeutic effect by adding topical carrier DMSO as adjuvant.

DETAILED DESCRIPTION OF THE INVENTION

It is known also that 2,2-dichloropropionic acid is daylight-sensitive and can transform into pyroracemic acid or eliminate HCl, followed by the production of alpha chloroacrylic acid during heating and prolonged storage:

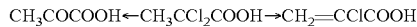

$$CH_3COCOOH \leftarrow CH_3CCl_2COOH \rightarrow CH_2{=}CClCOOH$$

It may decompose on exposure to moist air or water, is not compatible with oxidizing agents such as perchlorates, peroxides, permanganates, chlorates, nitrates and strong bases such as sodium hydroxide and potassium hydroxide.

Warranty storage life of the reagents grade product does not exceed 2 years.

The incoming inspection of starting raw materials has shown that the mass content of 2,2-dichloropropionic acid in commercial products does not exceed 80.0% practically. The main impurities are related acids: 2-chloropropionic acid and dichloroacetic acid (up to 5.0%), acetic acid, chlorine- and trichloroacetic acid, propionic acid, tri and tetra-chloropropionic acids, cis-chloroacrylic and pyruvic acids (the content of each varies from 0.05% to 1.0-2.0%), and a number of minor impurities at a rate of about 0.01%.

The identification of 2,2-dichloropropionic acid impurity, taken as an example, can be conducted by $^1H$ and $^{13}C$ NMR spectroscopy.

It is important to emphasize here that almost all of above acids in principle are acceptable impurities from the standpoint of the pharmacological action. Some of them and oxidation products thereof have keratolytic properties and according to the prior art are included in preparations useful for treating of skin diseases.

It is also known that selenious dioxide is an important reagent in organic synthesis and used for selective oxidation of activated $CH_2$-groups to $C{=}O$ group. This reaction is called the Riley oxidation. The $SeO_2$ is reduced to Se which precipitated as a red amorphous solid and easily can be filtered off.

Obviously, some of the above impurities can be oxidized with the selenium dioxide, in other words, can be the cause of chemical incompatibility between the components of the drug.

Therefore, the problem of Se-containing preparations stability is the liquidation of chemical incompatibility between selenious acid (or equivalents thereof) and those components of the medicinal agent that may be subjected to oxidation.

Methods to prepare 2,2-dichloropropionic acid of purity grade over 97% described in the prior art, such as an azeotropic distillation in deep vacuum at high efficiency column (U.S. Pat. Nos. 3,772,157 and 5,215,671) or the use of intermediates such as cyclohexylammonium (H. Holterman et al., *J. Org. Chem.* 1983, vol. 48, pages 4030-4035) or plumbic salts are difficult and expensive. Nevertheless, the use 2,2-dichloropropionic acid purified by these ways to prepare a stable Se-comprising compositions was unsuccessful.

It is known also that Se is dissolved in nitric acid to form selenious acid:

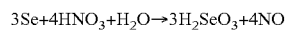

$$3Se+4HNO_3+H_2O \rightarrow 3H_2SeO_3+4NO$$

We hypothesized that this reaction could be used to dissolve Se formed for a long-time storage of the substance or pharmaceutical composition solutions. However, it is not confirmed: the reaction accompanied by eruption of heat, nitrogen oxides and carbon dioxide, but the Se dissolution not observed.

Surprisingly and unexpectedly, we found that addition of concentrated nitric acid into 2,2-di-chloropropionic acid, followed by addition of $H_2SeO_3$ that is used instead of $SeO_2$, leads not only to the formation of a very stable over a long-time storage pharmaceutical formulation but also dramatically increases the selenium content in solution.

The foregoing problems have been solved by the present invention and a technical advance is achieved by a new method of stable Se-comprising pharmaceutical composition production. The present disclosure provides a very surprising and highly effective method for preventing and minimization of Se precipitation for a long-time storage.

It is possible to agree that the term "stabilization" probably does not adequately reflect the nitric acid role but in practice any methods to preserve the appearance and destroy of the pharmaceutical composition are categorized as "stabilization".

The term "pharmaceutical composition", as used herein, describes a composition useful for the patient's healing.

The term "semi-finished product" or "pharmaceutical substance", as used herein, describes a concentrated pharmaceutical composition used for dosage forms preparation.

The term "dosage form", as used herein, describes a pharmaceutical composition useful for treating skin diseases comprising topical application thereof.

The percentage of ingredients, as used herein, are by weight.

Considering long-term experience of the containing nitric acid compositions application, and small amounts thereof that are required for stabilization of the present disclosure objects, it was possible to believe, that pharmacological properties of a preparation will not change. Special check has confirmed justice of this assumption.

At the initial stage of works in order to establish some fundamental properties of a substance (such as character and a direction of reactions of degradation), to identify the major products of disintegration and to select of the most suitable analytical techniques the method of stresses-tests was applied to definition of active agent and disintegration thereof at presence each other. It was expected, that results of such tests can show, how long the pharmaceutical substances and dosage forms are capable to maintain the short, but the extremely adverse conditions. Experiments spent at temperatures from 50 to 100° C. in the conditions of the raised humidity and an intensive uv-irradiation. Duration of experiment in most cases stole up so that to provide deep (to 50%) disintegration of studied substances.

According to the main and the most important aspect in preferred embodiments of the present disclosure is provided only certain order of the reactants mixing and the exact value of nitric acid content.

When $HNO_3$ is added into $CH_3CCl_2COOH$ before the adding of selenious acid Se does not precipitate again during for a long-time storing that indicates the redox process was blocked or strongly braked.

If the $HNO_3$ adding is less than 1.0%, a red or gray Se precipitates sooner or later again, if more than 5.0%, the solution colored in yellow, and this color remains for uncertain term.

According to the next important aspect of the present disclosure is provided the use of selenous acid solution instead of selenium dioxide.

The special experiments revealed that the using of an excess of selenium dioxide to oxidize 2,2-dichloropropionic acid impurity was unaffected. After the successive filtration Se precipitates from the clarified solution again, that indicates the incompleteness of the redox process.

The selenium dioxide solubility in concentrated 2,2-dichloropropionic acid solution is very low even at elevated temperatures and dissolution process leads to formation of a few unstable unidentified compounds.

According to the next point of the present disclosure is provided the interaction between $H_2SeO_3$ and an alpha, alpha-dichlorocarboxylic acid is conducted at temperature no higher than 70° C., preferably at 20-30° C. This way allows to avoid transform 2,2-dichloro-propionic acid into pyroracemic acid or alpha-chloroacrylic acid during heating and prolonged storage.

According to the another point of the present disclosure is provided the estimation that dichloroacetic, 2,2-dichlorobutyric acids and other members of the homologous series subjected to a similar stabilization can be used as an alternative to alpha, alpha-dichloropropionic acid.

According to the feature of the present disclosure is provided the adding of 5-20% dimethylsulfoxide (DMSO).

The intact skin of human is a very effective barrier to many natural or synthetic substances. Many of pharmaceutical agents are much less or totally ineffective on topical application to the skin that depends on two major factors
  a) boiavilability of the active ingredient in the topical preparation
  b) percutaneous absorption, penetration and distribution of the active ingredient to the target site of skin.

Although a simple aqueous solution of the pharmaceutical product prepared according the present disclosure is effective for a skin lesions treating well known topical carrier such as DMSO was used as a diluents and adjuvant to improve the physical consistency of the formulation and to provide the therapeutic effect. In some cases this way allows to reduce the period of treatment of skin diseases.

Dimethylsulfoxide is mixed with the preparation in every respect and less toxic compared with saline solution. Local application of DMSO and nutraceuticals (not pharmaceuticals) big molecular weight that hardly got through a skin is described in U.S. Pat. Appl. No. 2003/0109495 and U.S. Pat. No. 3,711,606.

The distinctive features and advantages of the new method of pharmaceutical products production according the present disclosure are:
  attendant impurities of 2,2-dichloropropionic acid are oxidized by nitric acid at isothermal conditions to form gaseous products ($CO$, $CO_2$, $NO$, $NO_2$) that are removed from the reaction mixture.
  use of the selenious acid instead of $SeO_2$ allows to avoid the formation of unstable to the moisture mixed anhydrides of 2,2-dichloropropionic and selenious acids, and Se is not precipitated during the warranty storage period drug.
  nitric acid as a more powerful oxidant compared with $H_2SeO_3$ almost complete suppresses the oxidizing power of selenious acid and ensures pharmaceutical product high stability.
  sufficiently simple technique to remove from the reacting system all of admixtures oxidized by the selenious acid,
  the pharmaceutical substance and the dosage form preserves stability for a long-time storage, that was unprecedented in prior art,
  the content of selenium in the pharmaceutical substance and the dosage form prepared according the present invention can be raised up to any reasonable values,
  selenium preservation in the pharmaceutical preparations prepared according the present invention provides the necessary therapeutic effect.

The present disclosure is illustrated by the following non-limiting examples:

EXAMPLES 2,2-Dichloropropionic acid density of $d_4^{20}$ 1.393-1.412 and purity grade not less than 98.5% is used.

Deionized water as an inert carrier was used as a diluents. The other conventional and well-known topical carries such as DMSO may be used.

Selenium dioxide crystallizes in needles or prisms and volatilizes when heated, giving a pale yellow vapour. It is very hygroscopic, and dissolves in water and alcohol.

Selenous (or selenious) acid, $H_2SeO_3$, structurally more accurately described by $(HO)_2SeO$ is the principal oxoacid of selenium. Oxidizing agents readily convert it into selenic acid, $H_2SeO_4$, whilst reducing agents transform it into selenium. It is decomposed by many acids with liberation of selenium. Selenous acid is easily formed upon the addition of selenium dioxide into water. It is moderately oxidizing in nature, but kinetically slow.

Several allotropic forms of selenium have been described. The amorphous variety, which only differs from the vitreous form in its state of aggregation, is obtained by reducing solutions of selenious acid. The grey crystalline form is obtained by heating the other varieties, and is the most stable form from ordinary temperatures up to 217° C.

Dosage forms include a liquid solution.

The dosage form solution was simply prepared by dissolving of the liquid pharmaceutical substances in water.

Example 1

Method of Pharmaceutical Products Producing According the Prior Art

Distilled water, 5 ml, and selenium dioxide, 0.66 g (0.006 g-mole) is adding into 2,2-dichloropropionic acid, 45 ml (62.5 g, 0.437 g-mole), and heating the substance at a temperature of 105° C. while stirring for 60 min., then cooling to room temperature and filtering off to obtain the semi-finished product (pharmaceutical substance) as yellow transparent solution. Quality parameters are: $d_4^{20}$ 1.362, 2,2-dichloropropionic acid—91.9%, water—7.8%.

When storing substance at 20-25° C., Se precipitates and after a week quality parameters are: $d_4^{20}$ 1.361, 2,2-dichloropropionic acid—92.0%, water—7.9%, selenium—0.03% instead of expected 0.7%.

When diluting the substance with distilled water to a concentration of 70%, red Se comes down as a red precipitate after 5 hours, turning gray in a few days. Quality parameters are: $d_4^{20}$ 1.278, 2,2-dichloropropionic acid content—70.5%, water—28.8%, selenium—0.03%. Change of concentration of selenium in a solution in time is presented in the table 1.

TABLE 1

| Storage time, days | Se, % | Storage time, months | Se, % |
|---|---|---|---|
| Original substance | 0.7 | 1 | 0.3 |
| 7 | 0.5 | 2 | 0.2 |
| 21 | 0.4 | 3 | 0.1 |

A number of special tests revealed that after storage of the pharmaceutical substance and dosage form signals of acetic and propionic acids in $^1H$ and $^{13}C$ NMR spectrum of solutions are absent, whereas signals of glyoxalic and oxalic acids do show up. The simultaneous precipitation of selenium is observed. After the successive filtration of selenium precipitation, it precipitates again from the clarified solution, which indicates the incompleteness of the redox process due to low speed thereof.

Example 2

Production of the Pharmaceutical Substance and the Dosage Forms According to the Present Invention. A Preferable Versue 60% nitric acid, 1.7 ml (2.3 g, 1.0%), was added into 2,2-dichloropropionic acid, 100 ml, with high speed mixing in a glass vessel equipped a propeller-type mixer and the solution was mixed well under isothermal conditions.

When the reaction was completed subsequently $H_2SeO_3$ solution obtained by dissolving of selenium dioxide, 1.435 g, in water, 10 ml, was added to result solution. The temperature was maintained at 20-25° C. for 8-12 hours with mixing or after the expiration of the 10 minutes period the solution was heated at the temperature of 50-60° for 3-6 hours. Finally the solution was cooled to room temperature and the result pharmaceutical substance was obtained as transparent yellow solution, 151.5 g. Quality parameters are: $d_4^{20}$ 1.386, 2,2-dichloropropionic acid—91.7%, of water—7.8%, of selenium—0.68%, nitrate ions—0.04%.

The substance is diluted with distilled water to 70% concentration and dosage form as a colorless solution is obtained. Quality parameters are: $d_4^{20}$ 1.279, 2,2-dichloropropionic acid—70.5%, of water—29.3%, of selenium—0.49%, nitrate ions—0.03%.

Other examples from this series are shown in the Table 2.

$^{77}Se$ NMR spectroscopy method proved the formation of a complex of selenious acid with 2,2-dichloropropionic acid.

It was found that if the water content in the pharmaceutical substance is less than 1.0%, then, out of 4 signals of low intensity with chemical shifts of 1116.4, 1040.8, 662.3 and 439.6 ppm only the first two can be reliably attributed to derivatives containing the arrangement Se=O and evidently representing mixed anhydrides of selenious and 2,2-dichloropropionic acid of formula $CH_3CCl_2COOSeO(OH)$ and $(CH_3CCl_2COO)_2Se=O$, and the last two signals apparently belong to mixed anhydrides complexes of selenious acid and 2,2-dichloropropionic acid.

Addition about of 10.0% water to the concentrated pharmaceutical substance leads to complete disappearance all of the 4 signals and to appearance of one intense signal at 1236 ppm. Compare: aqueous solution of selenious acid contains only one signal at 1279 ppm, and solution of selenious acid in 2,2-dichloropropionic acid contains only one signal at 1236 ppm. The shift of $^{77}Se$ signal of 43 ppm towards the stronger field indicates the interaction between those acids, that, apparently, is being accompanied by the complexes of structure $H_2SeO_3 \cdot x CH_3CCl_2COOH$ formation (coefficient x is not identified experimentally). No other changes have been detected in $^{77}Se$ NMR spectrum.

Example 3

The Preparation of the Substance with High Concentration of Selenium

The synthesis of the substance is conducted as Ex.2 with the only difference in the quantity of the selenious acid. The examples of this series are shown in the Table 3.

Example 4

The Preparation of the Medical Agent with High Permeability

Substance, 100 ml, obtained as Ex.2, is mixed with of dimethylsulfoxide, 10 ml, and diluted by distilled water to 70% concentration. Quality parameters are: $d_4^{20}$ 1.278, 2,2-dichloropropionic acid—70.3%, of water—29.5%, of selenium—0.49%.

The other examples of this series are shown in the Table 4.

Example 5

Preparation of the Pharmaceutical Substance and Dosage Forms

Influence of an Order of Components Mixing

A) 1.7 ml (2.3 g, 1.0%) of 60% nitric acid was added into $H_2SeO_3$ solution, obtained by dissolution $SeO_2$, 1,435 g, in water, 10 ml, under stirring, mix was stirred for 30-60 minutes at a temperature of 20-25° C. and then the result solution was added into 2,2-dichloropropionic acid, 100 ml. A light yellow solution quality parameters are: $d_4^{20}$ 1.386, 2,2-dichloropropionic acid—91.5%, water—7.8%, selenium—0.6%, nitrate ions—0.06%.

B) 2,2-dichloropropionic acid, 100 ml, was added into $H_2SeO_3$ solution obtained by dissolution $SeO_2$, 1,435 g, in water, 10 ml, under stirring, mix was stirred for 30-60 minutes at a temperature of 20-25° C. after that 1.7 ml (2.3 g, 1.0%) of 60% nitric acid was added. A light yellow solution quality parameters are: $d_4^{20}$ 1.386, 2,2-dichloropropionic acid—91.7%, water—7.7%, selenium—0.6%, nitrate ions—0.05%.

C) $H_2SeO_3$ solution, obtained by dissolution $SeO_2$, 1,435 g, in water, 10 ml, was added under stirring at a temperature of 20-25° C. into 2,2-dichloropropionic acid, 100 ml, mix was stirred for 30-60 minutes at a temperature of 20-25° C. after that 1.7 ml (2.3 g, 1.0%)

of 60% nitric acid was added. A light yellow solution quality parameters are: $d_4^{20}$ 1.386, 2.2-dichloropropionic acid—91.6%, water—7.7%, selenium—0.6%, nitrate ions—0.06%.

D) A preferable versue. 1.7 ml (2.3 g, 1.0%) of 60% nitric acid was added into 2,2-dichloropropionic acid, 100 ml, under stirring at a temperature of 20-25° C., mix was stirred for 30-60 minutes at a temperature of 20-25° C. after that $H_2SeO_3$ solution obtained by dissolution $SeO_2$, 1,435 g, in water, 10 ml, was added. A light yellow solution quality parameters are: $d_4^{20}$ 1.386, 2.2-dichloropropionic acid—91.7%, water—7.8%, of selenium—0.6%, nitrate ions—0.05%.

The pharmaceutical substance solutions obtained as exp.5a-d part at once were planted with the distilled water to 70% concentration. Practically colorless solution quality parameters are: $d_4^{20}$ about 1.28, 2.2-dichloropropionic acid—about 70.0%, water—about 30.0%, of selenium—about 0.5%, nitrate ions—from about 0.5% to about 1.0%.

At storage of pharmaceutical substance solution obtained as exp.5 a-c grey Se precipitated and level thereof in solutions decreased up to 0.05-0.1%.

At storage of pharmaceutical substance solution obtained as exp.5d under the same conditions Se not precipitated from solution and level thereof in solutions retained on start level.

Example 6

Aging of the Semi-Finished Product and Dosage Forms Under Isothermal Conditions

The results of this series are shown in Table 5

Example 7

The Preparation of Pharmaceutical Product with High Concentration of Selenium Based on Dichloroacetic Acid 1.7 ml (2.3 g, 1.0%) of 60% nitric acid was added into 2,2-dichloroacetic, 100 ml, under stirring at a temperature of 20-25° C., mix was stirred for 30-60 minutes at a temperature of 20-25° C. after that $H_2SeO_3$ solution, obtained by dissolution $SeO_2$, 1,435 g, in water, 10 ml, was added. A light yellow solution quality parameters are: 2.2-dichloroacetic acid—92.3%, water—7.8%, of selenium—0.6%, nitrate ions—0.05%.

At long-time storage of pharmaceutical substance Se not precipitated from solution and level thereof in solutions retained on start level.

TABLE 2

Synthesis of the semi-finished product and pharmaceutical product, stabilized by the nitric acid additions

| No | Content HNO$_3$, % | Synthesis temperature, °C | $d_4^{20}$ | 2,2-DCPA, % | Se, % | NO$_2$, % |
|---|---|---|---|---|---|---|
| Semi-finished Product Synthesis ||||||||
| 2-1 | 1 | 20 | 1.386 | 92.7 | 0.68 | 0.04 |
| 2-2 | 1 | 50 | 1.385 | 92.5 | 0.68 | 0.04 |
| 2-3 | 1 | 70 | 1.387 | 92.6 | 0.67 | 0.04 |
| 2-4 | 3 | 20 | 1.387 | 93.4 | 0.69 | 0.08 |
| 2-5 | 3 | 50 | 1.388 | 93.2 | 0.70 | 0.09 |
| 2-6 | 3 | 70 | 1.388 | 93.2 | 0.67 | 0.09 |
| 2-7 | 5 | 20 | 1.386 | 95.5 | 0.69 | 0.13 |
| 2-8 | 5 | 50 | 1.386 | 95.3 | 0.65 | 0.11 |
| Pharmaceutical Product Synthesis ||||||||
| 2-9 | From the semi-finished product 2-1 | 20 | 1.279 | 70.5 | 0.48 | 0.03 |
| 2-10 | From the semi-finished product 2-6 | 20 | 1.279 | 70.0 | 0.47 | 0.04 |
| 2-11 | From the semi-finished product 2-8 | 20 | 1.279 | 70.8 | 0.46 | 0.04 |

TABLE 3

The synthesis of the semi-finished product with the high concentration of selenium.

| No | H$_2$SeO$_3$, % | $d_4^{20}$ | 2.2-DCPA, % | Water, % | Se, % | NO$_3^-$, % |
|---|---|---|---|---|---|---|
| 3-1 | 0.5 | 1.390 | 92.5 | 7.5 | 0.32 | 0.04 |
| 3-2 | 1 | 1.391 | 92.7 | 7.5 | 0.61 | 0.04 |
| 3-3 | 2 | 1.386 | 91.3 | 8.0 | 1.23 | 0.04 |
| 3-4 | 5 | 1.387 | 91.1 | 8.5 | 3.05 | 0.05 |
| 3-5 | 10 | 1.390 | 92.1 | 7.6 | 6.15 | 0.04 |
| 3-6 | 16 | 1.394 | 92.6 | 7.3 | 9.81 | 0.03 |
| 3-7 | 20 | 1.393 | 91.8 | 7.9 | 12.26 | 0.05 |

TABLE 4

The synthesis of the medical agent with high permeability

| No | (CH$_3$)$_2$SO, % | HNO$_3$ in the semi-finished product, % | H$_2$SeO$_3$ in the semi-finished product, % | $d_4^{20}$ | 2,2-DCPA, % | Se, % | NO$_3^-$, % |
|---|---|---|---|---|---|---|---|
| 4-1 | — | 1 | 0.5 | 1.279 | 70.2 | 0.21 | 0.05 |
| 4-2 | 20 | 3 | 1 | 1.278 | 70.0 | 0.48 | 0.04 |
| 4-3 | 20 | 5 | 2 | 1.278 | 70.3 | 0.85 | 0.04 |
| 4-4 | 20 | 1 | 5 | 1.280 | 70.1 | 2.15 | 0.04 |
| 4-5 | 10 | 3 | 10 | 1.283 | 70.1 | 4.31 | 0.05 |
| 4-6 | 5 | 3 | 20 | 1.288 | 70.2 | 8.59 | 0.03 |

TABLE 5

The solution stability of the semi-finished product and pharmaceutical product under extended storage conditions

| No | Temperature, ° C. | Duration | Monitored solution | Physical Configuration | $d_4^{20}$ | $H_2O$, % | 2,2-DCPA*, % | Se, % | $NO_3^-$, % |
|---|---|---|---|---|---|---|---|---|---|
| 1 | 20-25 | 3 mo | Semi-finished product prior art | settling precipitated | 1.361 | 7.9 | 92.0 | 0.03 | — |
| 2 | 20-25 | 5 hrs | pharmaceutical product prior art | settling precipitated | 1.278 | 28.8 | 70.5 | 0.03 | — |
| 3 | 20-25 | 2 yr | Semi-finished product 2-1. 1% $HNO_3$ | no change. no settling | 1.386 | 7.5 | 92.7 | 0.68 | 0.03 |
| 4 | 50 | 9 mo | Semi-finished product 2-6. 3% $HNO_3$ | no change, no settling | 1.387 | 6.7 | 93.2 | 0.69 | 0.08 |
| 5 | 50 | 9 mo | Semi-finished product 2-8, 5% $HNO_3$ | no change. no settling | 1.386 | 4.6 | 95.3 | 0.65 | 0.11 |
| 6 | 20-25 | 2 yr | pharmaceutical product 2-9 | no change. no settling | 1.279 | 29.3 | 70.5 | 0.48 | 0.03 |
| 7 | 20-25 | 2 mo | pharmaceutical product 2-10 | no change, no settling | 1.279 | 29.7 | 70.0 | 0.47 | 0.04 |
| 8 | 50 | 9 mo | pharmaceutical product 2-11 | no change. no settling | 1.279 | 29.2 | 70.8 | 0.46 | 0.04 |
| 9 | 20-25 | 2 yr | Semi-finished product 3-4. 5% $H_2SeO_3$ | no change. no settling | 1.393 | 3.6 | 93.5 | 3.05 | 0.03 |
| 10 | 50 | 9 mo | Semi-finished product 3-5. 10% $H_2SeO_3$ | no change, no settling | 1.393 | 7.5 | 92.1 | 7.6 | 0.04 |
| 11 | 20-25 | 2 yr | Semi-finished product 3-6, 20% $H_2SeO_3$ | no change, no settling | 1.395 | 8.0 | 91.8 | 7.9 | 0.05 |
| 12 | 50 | 9 mo | pharmaceutical product 4-1 | no change, no settling | 1.278 | 29.5 | 70.2 | 0.65 | 0.04 |
| 13 | 20-25 | 2 yr | pharmaceutical product | no change, no settling | 1.278 | 29.4 | 70.3 | 1.32 | 0.04 |
| 14 | 20-25 | 2 yr | pharmaceutical product 4-3 | no change, no settling | 1.280 | 29.4 | 70.5 | 1.33 | 0.04 |
| 15 | 20-25 | 2 yr | pharmaceutical product 4-5 | no change, no settling | 1.283 | 29.5 | 70.1 | 4.31 | 0.05 |
| 16 | 50 | 2 mo | pharmaceutical product 5a | settling precipitated | 1.277 | 30.5 | 70.2 | 0.05 | 0.03 |
| 17 | 50 | 2 mo | pharmaceutical product 5b | settling precipitated | 1.276 | 30.5 | 70.5 | 0.03 | 0.04 |
| 18 | 50 | 2 mo | pharmaceutical product 5c | settling precipitated | 1.277 | 29.8 | 70.3 | 0.07 | 0.04 |
| 19 | 50 | 30 mo | pharmaceutical product 5d | no change, no settling | 1.278 | 29.5 | 70.2 | 0.65 | 0.05 |
| 20 | 50 | 3 mo | pharmaceutical substance 7 | no change, no settling | 1.357 | 7.8 | 92.3 dcac8 | 0.6 | 0.05 |

*DCPA = 2,2-dichloropropionic acid
*dcac = dichloroacetic acid

Clinical Trials

As medicinal agent for the topical skin applications the dosage form solutions comprising about 70% 2,2-dichloropropionic acid, selenious acid from about of 0.05 to about of 0.5% Se, nitric acid from about of 0.005 to about of 0.02% as nitrite-ions and water forming the balance as diluents or carrier is used or, alternatively, a preparation with an additive of 5-20% dimethylsulfoxide as topical carrier is used.

According to the clinical trials 25 patients (5 men and 20 women, aged 29 to 79) were assigned to group A which diagnosed with the "primary basal cell carcinoma (BCC), stage T1N0M0" and 100 patients (25 men and 75 women, aged 18 to 86) assigned to group B which diagnosed with multiple papilloma, seborrheic keratosis, angiomas, papillomatous nevi and cutaneous horn. The diagnosis was confirmed by the results of the cytological screening.

Aliphatic alpha-haloidcarboxylic acids and related compounds further application for the treatment more than 70 nosologies skin disease described in our most recent RU 2366648 entitled "The product of interaction between selenious dioxide and aliphatic haloid carboxylic acids, the method of production preparation and the method of treatment of benign, viral, premalignant, and malignant non-metastasizing skin lesions, of dysplastic lesions of visible mucous coats, fungous and other skin diseases".

The out-patient treatment was without anesthesia application. The preparation was applied to lesion foci (after the preliminary treatment with 70% ethanol) with a plastic spatula or a glass capillary, covering additional 1-2 mm of healthy skin. The anatomical structure is intravitally fixed without injury (mummification).

The dosage of the preparation depends on the stage, clinical form of the disease and the density of the tumor, though usually the single curative dose did not exceed 0.2 ml. The treatment period is 1 course (3 weeks).

The healing process goes without complications or without leaving any significant scars, cicatrices or deformations of adjacent tissues, or any damages to internal functions. At the end of the therapeutic course a thorough observation of tissues takes place after complete mummified scab has been rejected, and if there is a suspicion of the incompleteness of the treatment an additional application may be prescribed by the doctor.

In assessing the overall status (blood pressure, pulse rate, temperature), no indexes of clinical and blood biochemical parameters of statistically significant changes after treatment were found. The long term results of the treatment were assessed 3 and 6 months after the first application. There were also no registered cases of therapeutic course interruption due to the development of any apparent toxicity (pain syndrome, skin toxicity) and/or any other negative effects related to the preparation application. Disease relapses were not registered too. More rapid restoration of the physiological coloring of skin integument was shown when the preparation was used with addition of dimethylsulfoxide.

No pathological changes in tumors, or significant changes in the results of clinical and biochemical blood tests, or any relapse after conducted treatment were statistically observed. The result of the clinical trials demonstrate significant positive changes in skin conditions in all terms.

Therefore, the clinical examination showed that the external application of the preparation arrests the proliferation of pathologically changed cells, provides for direct intravital fixation with the following mummification of pathologically changed tissue, doesn't leave any deep or interfacial cicatrices, is well tolerated by the patients.

The pharmaceutical product is recommended for a wide usage in practical medicine for the removal of benign skin neoplasms: papillomatous nevuses, seborrheic keratosis, cutaneous horn, papillomatous benign skin disease caused by HPV, vascular benign skin disease and also in case of the relapses of these neoplasms after surgical, cryo- or laser treatment.

The invention is claimed as follows:

1. A method of preparing a stable pharmaceutical selenium-containing composition useful for treatment of skin diseases and comprising therapeutically effective amounts of at least two active ingredients selected from the group consisting of: alpha, alpha-dichlorocarboxylic acids, a selenium-containing compound, and a combination thereof, wherein the selenium-containing compound is selenious acid comprising:
   adding nitric acid into an alpha, alpha-dichloropropionic acid;
   completing the redox-interaction under isothermal conditions at a temperature not higher than 70° C.; and
   adding an aqueous solution of the selenious acid in an amount of not more than 20.0% to form the resultant pharmaceutical product solution.

2. The method of preparing a stable pharmaceutical selenium-containing composition of claim 1, wherein alpha, alpha-dichlorocarboxylic acid is 2,2-dichloropropionic acid.

3. The method of preparing a stable pharmaceutical selenium-containing composition of claim 1, wherein alpha, alpha-dichlorocarboxylic acid is dichloroacetic acid.

4. The method of preparing a stable pharmaceutical selenium-containing composition of claim 1, wherein the composition comprises 1-3% nitric acid.

5. The method of preparing a stable pharmaceutical selenium-containing composition of claim 1, wherein the composition comprises 0.5-10.0% selenious acid.

6. The method of preparing a stable pharmaceutical selenium-containing composition of claim 1, wherein the chemical interaction between alpha, alpha-dichlorocarboxylic acid and nitric acid is carried out at temperature of 20-30° C.

* * * * *